United States Patent [19]

Green

[11] Patent Number: 4,897,035

[45] Date of Patent: Jan. 30, 1990

[54] CONNECTOR APPLIANCE FOR ORTHODONTIC APPLIANCE SYSTEMS

[76] Inventor: William A. Green, 488 Beech St., San Bruno, Calif. 94096

[21] Appl. No.: 237,854

[22] Filed: Aug. 29, 1988

[51] Int. Cl.$^4$ .............................................. A61C 7/00
[52] U.S. Cl. ...................................................... 433/17
[58] Field of Search ......................................... 433/17

[56] References Cited

U.S. PATENT DOCUMENTS

| 1,429,749 | 9/1922 | Maeulen et al. | 433/17 |
| 3,250,003 | 5/1966 | Collito | 433/9 |
| 3,303,565 | 2/1967 | Newman | 433/9 |

*Primary Examiner*—Robert Peshock
*Attorney, Agent, or Firm*—Owen, Wickersham & Erickson

[57] ABSTRACT

An orthodontic appliance system includes a plurality of connector appliances for rigidly connecting a force-supplying appliance to a patient's teeth to be positioned or stabilized. Each connector appliance includes a male connector piece rigidly attached to the force-supplying appliance and a female connector piece adapted for rigid attachment to a tooth to be positioned or stabilized. Each male connector piece is substantially wedge-shaped having a large base connected to the force-supplying appliance and a relatively narrow outer end. Each female connector piece includes a wedge-shaped receptacle generally corresponding in shape to the wedge shape of the male connector pieces, the receptacle being adapted to receive one of the male connector pieces in a fully inserted, connected position with the receptacle surfaces substantially abutting said wedge-shaped male connector. Each connector preferably also includes a locking device for locking the male and female pieces together in the connected position. The preferred locking means includes a spring loaded lever on the male connector piece with a projection that is adapted to be received in an aperture of the female connector piece when said connector pieces are in the connected position.

13 Claims, 5 Drawing Sheets

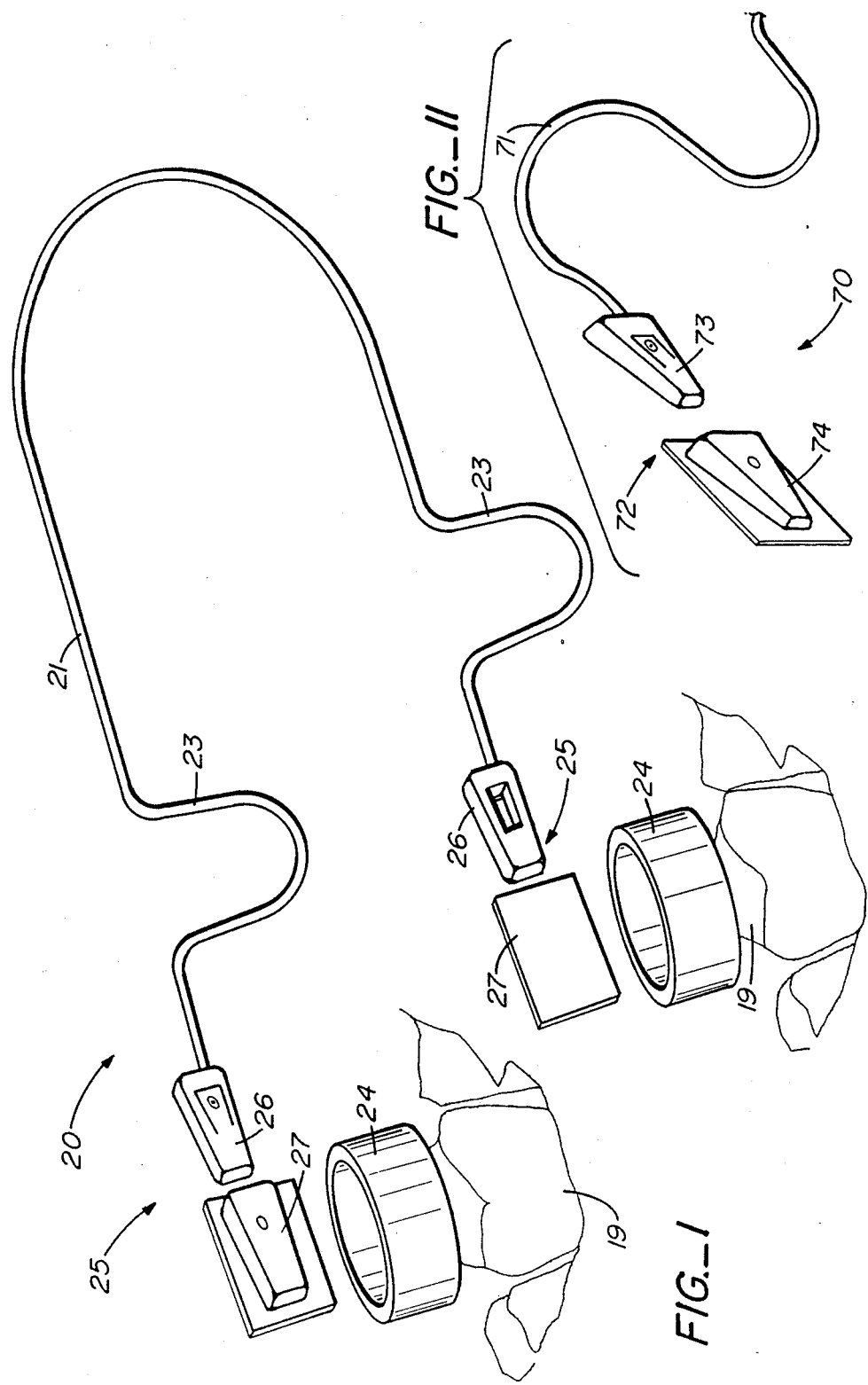

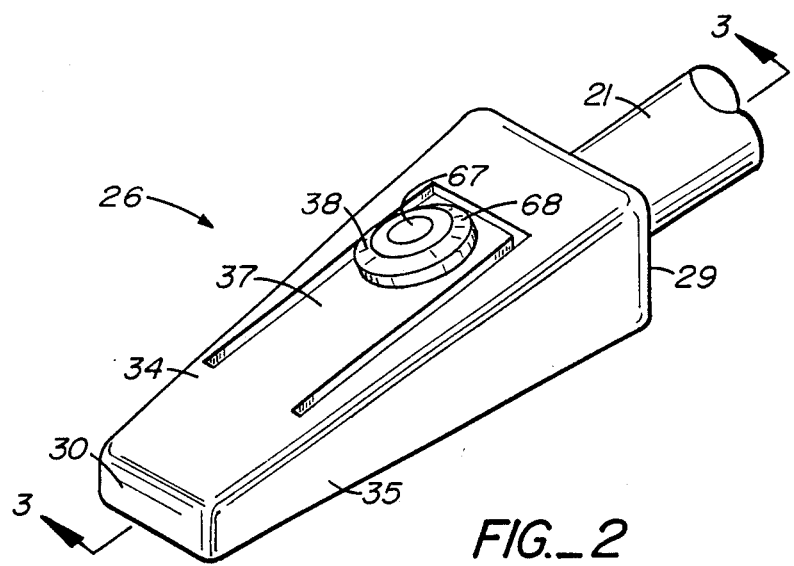
FIG._2
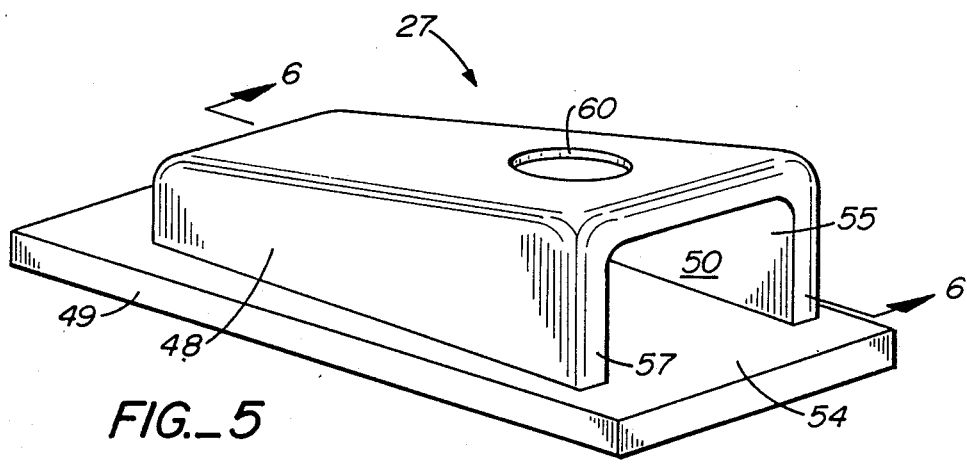
FIG._5

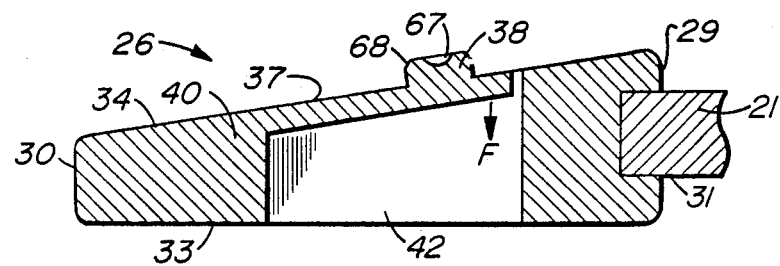
FIG._3
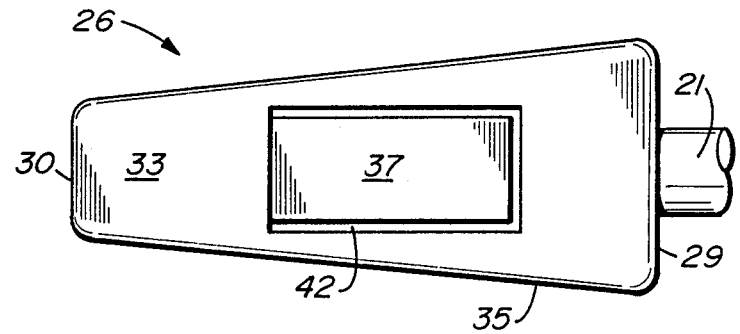
FIG._4
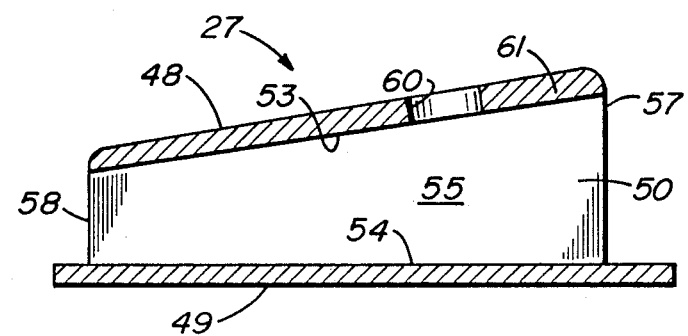
FIG._6

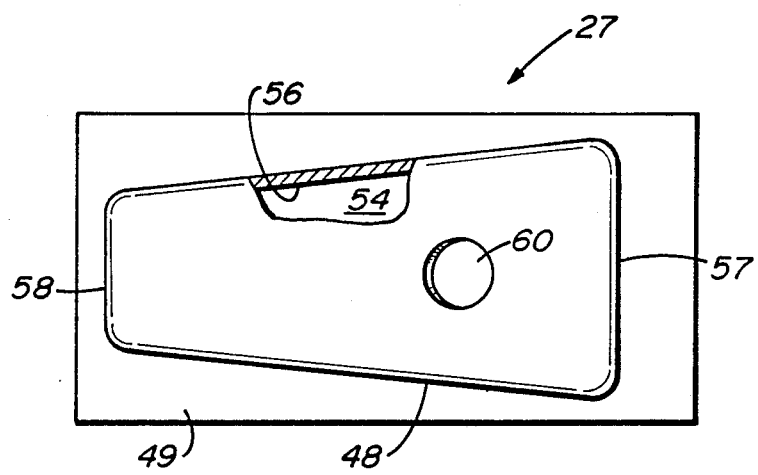
FIG._7
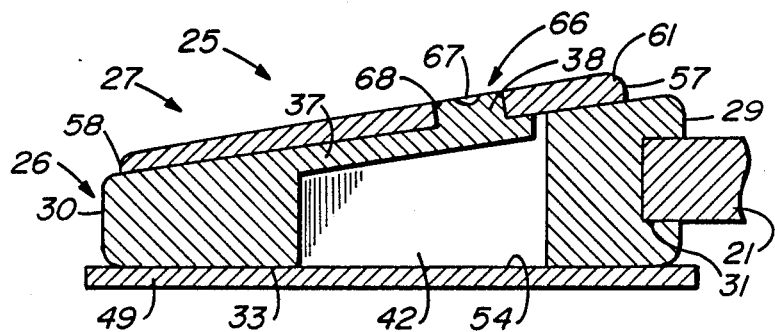
FIG._9
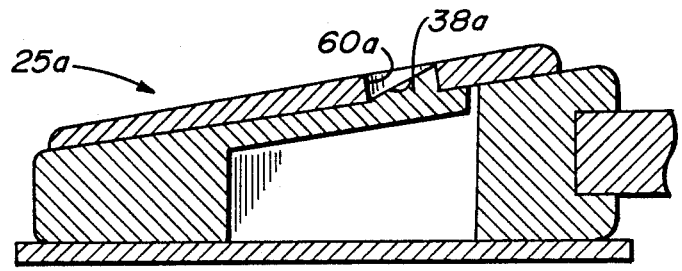
FIG._9A

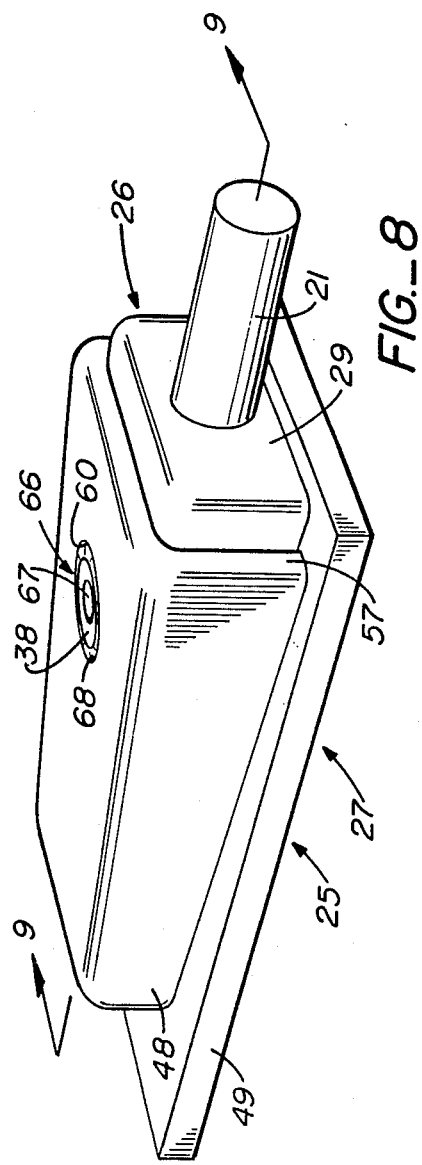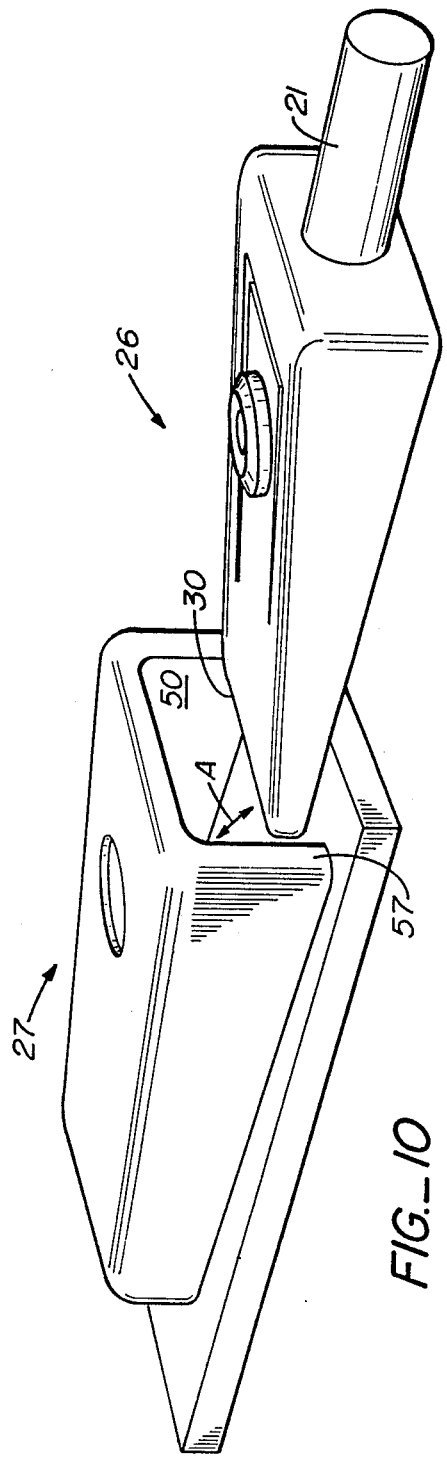

CONNECTOR APPLIANCE FOR ORTHODONTIC APPLIANCE SYSTEMS

This invention relates to orthodontic appliance systems, and particularly, to a connector appliance for enabling easy connection of an appliance system to a patient's teeth.

BACKGROUND OF THE INVENTION

Misaligned teeth are commonly realigned by applying a desired corrective force with a set of cooperating orthodontic appliances that are generally adapted to fit in the patient's mouth and to be worn for a period of time. Properly aligned teeth may also be stabilized with such orthodontic appliance systems. Much of the desired corrective or stabilizing force is applied with intra-oral appliances that are attached with connecting appliances to the buccal side of the tooth, that is, the side of the tooth adjacent to the cheek. However, some corrective force may be applied with auxiliary appliance systems that attach, directly or indirectly, to the patient's tooth on the lingual side, that is, the side of the tooth adjacent to the tongue.

Appliance systems for applying a desired force to a patient's teeth generally include a substantially rigid force-supplying appliance or member for supplying the desired force, and a plurality of connector appliances for rigidly attaching the force-supplying appliance to the particular teeth. Prior connectors comprised generally a connector sheath, tube, or channel adapted to be rigidly attached to a tooth and to receive and connect with a specially adapted portion of the force-supplying member. Generally, the connector sheaths or tubes were each attached to a band that fitted tightly around the tooth to be positioned; however, in some cases the sheaths or tubes were attached directly to the tooth by a suitable adhesive. Where no corrective force is applied by the force-supplying member, the connection between the force-supplying member and sheath or tube is said to be "passive," whereas, where corrective force is applied, the connection is said to be "active."

Common intra-oral auxiliary force-supplying appliances include palatal bars that extend transversely across the patient's palate for applying a desired force to the upper teeth, and lingual arches, which fit closely on the lingual side of the patient's teeth forming generally an arch shape to avoid interference with the patient's tongue.

Some prior orthodontic appliance systems used force-supplying members made of round wire. The ends of the members had a male connector, generally comprising a doubled wire section, that is, two side-by-side pieces of round wire. This doubled round wire connector end was adapted to fit tightly into a sheath having a generally rectangular, box-shaped receptacle. Connecting the force-supplying member to a particular tooth involved inserting the connector end of the force-supplying member into the sheath that had previously been attached to the particular tooth, and then tying the connector in place with a suitable ligature wire.

Other prior appliance systems had tubular sheaths, or tubes, for receiving a single round wire of the force-supplying appliance. With these round wire and tube connections, the force-supplying round wire member was usually required to have a control cross member, which could be tied to the tube for providing a desired rotational and torquing corrective force.

Some orthodontic appliance systems used a square wire force-supplying member that was adapted to be tied into a generally square channel connector that was attached to the tooth to be positioned or stabilized. This square-wire system provided some advantage in that the square wire and channel connection provided better rotational force control, and in many cases, much of the corrective force required to realign a tooth is rotational or torquing force.

There were a number of problems associated with the prior tooth-positioning systems. One such problem was that, where the force-applying member was a round wire, and the sheath receptacle generally rectangular, precise rotational force control was not possible because of the somewhat sloppy fit of the rounded wire in the rectangular receptacle, even when the round wire was doubled. The use of a control bar for helping control rotational force only partially compensated for the sloppy fit between the sheath and the force-supplying member.

Another problem was that each of the prior systems required that the force-supplying member be tied to the connector sheath or tube with a suitable ligature wire to provide a secure connection. The process of tying ligature wire was very time consuming and generally unpleasant for the patient. Furthermore, the sheaths often needed extra tying bars to facilitate tying.

With any of the prior rectangular sheath or square channel connector appliances, whether the force-supplying members were made of round wire or square wire, active connections were difficult because the connector end or portion of the force-supplying member had to be angled somewhat with respect to the sheath receptacle or channel prior to connection, in order to provide the desired force. That is, the fit between the force-supplying member connector end or connecting portion and the sheath or channel had to be as tight as possible to facilitate rotational control, yet the connector of the force-supplying member had to be angled prior to connection to apply the desired force. As a result, it was often very time consuming to make the desired active connection between the force-supplying member and the sheath or channel.

It is therefore an object of the invention to provide an orthodontic appliance system with a connector appliance that facilitates easy connection between the force-supplying member and the teeth to be positioned or stabilized.

Another object of the invention is to provide a connector appliance for orthodontic appliance systems that is easy to connect, yet provides good corrective force control, particularly, rotational force control.

Another object of the invention is to provide a connector appliance for orthodontic appliance systems, that locks into a connected position without the need for tying a ligature wire, and that may be easily released from the locked connected position.

These and other objects will be apparent from the following summary and description of the preferred embodiment, with reference to the drawings.

SUMMARY OF THE INVENTION

An orthodontic appliance system according to the invention includes a force-supplying member or appliance and a plurality of specially adapted connector appliances.

The force-supplying member is adapted to fit inside a patient's mouth for providing a desired force to the teeth to be positioned or stabilized. The connectors are adapted for rigidly connecting the force-supplying member to the desired teeth, the connectors comprising a generally wedge-shaped male connector piece and a female connector piece having a wedge-shaped receptacle for receiving the male connector piece.

The force-supplying member is preferably made of a substantially rigid material that enables the member to be bent into a desired configuration for supplying the necessary force to the particular teeth. Any type of force-supplying member may be used according to the invention, including intra-oral appliances such as palatal bars and lingual arches. Also, the force-supplying member may be adapted for applying force either to the buccal or lingual side of a patient's teeth.

A connector pursuant to the invention includes a male connector piece having a unique wedge shape and a female connector piece having a receptacle with a corresponding wedge shape for receiving the male connector piece. Each female connector piece is adapted to be rigidly attached to one of the patient's teeth, while each male connector piece is adapted to be rigidly attached to the particular force-supplying member being used. With the female connector piece attached to a tooth and the male connector attached to the force-supplying member, the two connector pieces are adapted to rigidly connect together, thereby connecting the force-supplying member to the particular tooth so that the force-supplying member can apply the desired force. The unique complementing wedge shapes of the male connector piece and the receptacle of the female connector piece enables the two pieces to be easily connected together to provide superior control of corrective force, particularly rotational and torquing force.

A male connector piece according to the invention is preferably made of a substantially rigid material and is generally wedge-shaped. Each male connector piece includes a large base end, preferably adapted to be connected to the force-supplying member, and a relatively narrow outer end. In one form of the invention each male connector piece has, in addition to the base and outer ends, four generally planar outer surfaces, a proximal surface and a distal surface which are opposite to each other, and two opposing outer side surfaces. To form the wedge shape according to the invention, the opposite proximal and distal surfaces are nonparallel, sloping together toward the relatively narrow outer end of the male connector piece. Also, the two opposing outer side surfaces are nonparallel and slope together toward the narrow outer end of the male connector. In this preferred form, the periphery of each outer surface forms generally a trapezoid.

In other forms of the invention, the male connector piece may have a triangular body shape having only three outer surfaces in addition to the two ends. Also, the male connector piece may have more than four outer surfaces pursuant to the invention. However, in any form, the generally opposing outer surfaces slope together from the base end to the outer end so that the outer end is narrower than the larger base end in each dimension.

A female connector piece according to the invention is adapted to rigidly attach to a patient's tooth either directly or indirectly and is also adapted to receive one of the male connector pieces, thereby rigidly connecting the force-supplying member to the tooth.

Each female connector piece includes a body having a generally wedge-shaped receptacle for receiving a male connector piece, the receptacle shape substantially corresponding to the wedge shape of the male connector piece. The receptacle of the female connector piece includes a large open end and a relatively narrow open end, corresponding to the base and outer ends, respectively, of the male connector. The receptacle also includes generally planar surfaces corresponding to the outer surfaces of the male connector piece, so that when the male connector piece is fully inserted in the receptacle to a connected position, the outer surfaces of the male connector piece and the inner surfaces of the receptacle closely abut each other. Thus, when the male connector piece is fully inserted to the connected position, there is substantially no room for lateral or twisting movement between the male connector piece and the female connector piece.

In the preferred form of the invention, each female connector receptacle includes two side surfaces corresponding to the outer side surfaces of the male connector, and an inner proximal and a distal surface corresponding respectively to the outer proximal and distal surfaces of the male connector.

The absence of substantial play between the two pieces of the connector and the plane on plane abutment facilitate very good control over the amount of rotational force supplied to a particular tooth. The practitioner need not account for substantial play in the connection between the force-supplying member and the tooth, as was necessary with the prior doubled round wire/rectangular sheath connectors.

The wedge shape of the female receptacle and the male connector piece also enables the practitioner to make an active connection between the force-supplying member and the tooth with relative ease, even where a substantial rotational corrective force is to be applied to the particular tooth. This ease of connection arises because the male connector piece enters the receptacle of the female connector piece, narrow outer end first, at the relatively large open end of the receptacle that corresponds to the large base end of the male connector. Thus, the male connector piece can be started into the receptacle of the female connector very easily even if the narrow end of the male connector piece is rotated somewhat, or cocked at some angle with respect to the female connector receptacle. As the male connector piece is inserted further, the two pieces are automatically brought into alignment, and the desired corrective force is applied to the tooth.

According to the invention, the male and female connector pieces of the connector appliance may be secured together in any suitable manner, for example with a ligature wire. However, the preferred connector appliance also includes a novel locking means for positively locking the two connector pieces together in the fully inserted, connected position.

In the preferred form, the locking means includes a spring-loaded lever, which may form generally a portion of the distal surface of the male connector piece. One end of the lever is attached to the male connector piece, and its other opposite end is free to flex inwardly into an open area in the male connector. A locking projection is positioned at the free end of the lever, the projection being biased by the lever in a position projecting somewhat away from the distal surface of the male connector piece. In this form of the invention, the locking means also includes an aperture or opening extending through a distal wall of the female connector piece. The aperture is positioned in the distal wall so that when the male connector piece is fully inserted to the connected position in the female connector piece receptacle, the locking projection snaps into the aperture, thereby locking the two connector pieces together without the need for tying with ligature wire.

In order to release the male connector, the locking projection may simply be depressed out of the aperture and the male connector piece withdrawn. The locking projection may be depressed with any of a variety of dental and orthodontic instruments.

BRIEF DESCRIPTION OF THE DRAWINGS

FIG. 1 is an exploded, partially diagrammatic view in perspective, and drawn to an enlarged scale, of an orthodontic appliance system embodying the principles of the invention.

FIG. 2 is a view in perspective, of one the male connector pieces shown in FIG. 1, drawn to a greater enlarged scale.

FIG. 3 is a view in section of the male connector piece taken along line 3—3 in FIG. 2.

FIG. 4 is a bottom plan view of the male connector piece shown in FIG. 2.

FIG. 5 is a view in perspective, drawn to a greatly enlarged scale, of a female connector piece embodying the principles of the invention.

FIG. 6 is a view in section of the female connector piece taken along line 6—6 in FIG. 5.

FIG. 7 is a top plan view of the female connector piece of FIG. 5.

FIG. 8 is a view in perspective, and drawn to a greatly enlarged scale, of a connector embodying the principles of the invention shown in the connected position.

FIG. 9 is a view in longitudinal cross-section taken along line 9—9 in FIG. 8.

FIG. 9A is a view in longitudinal cross-section similar to FIG. 9 of an alternate embodiment of the invention.

FIG. 10 is a view in perspective, and drawn to a greatly enlarged scale, of a connector embodying the principles of the invention, the male connector piece being only partially inserted in the female connector piece, and at a slight angle with respect to the female connector.

FIG. 11 is a partially diagrammatic view in perspective, and drawn to an enlarged scale, showing an alternate orthodontic appliance system embodying the principles of the invention.

DESCRIPTION OF THE PREFERRED EMBODIMENTS

FIG. 1 shows an orthodontic appliance system 20 embodying the principles of the invention. The appliance system 20 includes a force-supplying appliance or member 21, which, in this form of the invention, is a lingual arch having adjusting loops 23. The appliance system 20 also includes two connector appliances 25, each connector including a male connector piece 26 and a female connector piece 27. The connector appliances 25 and force-supplying member 21 may be made of any suitable, substantially rigid material, including stainless steel alloys developed specifically for orthodontic appliances, and also suitable plastics.

The force-supplying member 21, is adapted to fit inside a patient's mouth around the arch formed by the teeth. Each female connector piece 27 is adapted to be rigidly attached to a tooth 19 to which a desired force is to be applied by the force-supplying member 21. Each male connector piece 26 is rigidly attached to the member 21.

To connect the appliance system 20 to the patient's teeth, each female connector piece 27 is first rigidly attached to a tooth to which a desired force is to be applied. In each case the appliance system according to the invention will be connected to at least two of the patient's teeth, and thus will require two sets of connectors 25 as shown; however, other systems may connect to several teeth. The illustrated female connectors 27 are adapted to be attached by some suitable means to a band 24, and then the band 24, with the attached connector 27, is fitted tightly over a tooth 19. Although the bands 24 are shown in this illustrated system, direct attachment of the female connectors to the teeth with a suitable adhesive may be possible under certain circumstances. Once each female connector piece 27 is in position on its respective tooth 19, the orthodontist connects the force-supplying member 21 to each tooth 19 by inserting each male connector piece 26 into one of the female connector pieces 27 to a connected position (shown in FIGS. 8 and 9). Generally, each connector 25 is connected separately, the practitioner first making one connection and then moving on the other connectors 25 until each is in the connected position.

FIGS. 2, 3, and 4 show a male connector piece 26 for orthodontic connector appliances according to the invention. The male connector piece 26 is generally wedge-shaped and includes a large base end 29 and a relatively narrower outer end 30. The male end connector 26 is rigidly attached to the force-supplying member 21, preferably at its relatively large base end 29. Although any suitable means of attaching the male connector piece 26 to the force-supplying member 21 may be used, the two are preferably soldered or welded, together. To substantially eliminate the need for a jig, the base end 29 preferably includes an opening 31 (FIG. 3) for receiving some portion of the force-supplying member 21 to be soldered or welded in place.

The male connector piece 26, illustrated in FIGS. 2, 3, and 4, also includes four substantially planar outer surfaces, a proximal surface 33, a distal surface 34, and two opposing side surfaces 35. The male connector piece 26 being generally wedge-shaped, the proximal surface 33 and the distal surface 34, which are opposite each other, are nonparallel and slope together towards the relatively narrow outer end 30 of the connector piece 26. The two opposing side surfaces 35 are also nonparallel and slope together from the base end 29 toward the relatively narrower outer end 30. Also, all of the edges where the outer surfaces of the connectors 26 meet are preferably rounded somewhat.

The illustrated male connector piece 26 also includes a lever 37 which forms generally a portion of the distal surface 34. At the free end of the lever 37, a locking projection or knob 38, having an indentation 67 and bevelled upper edges 68, extends outwardly from the lever 37. The lever 37 and projection 38 form a portion of one preferred form of a locking means for locking the two connector pieces 26 and 27 (FIG. 1) together in the connected position. The operation of the locking means is described hereinafter with reference to FIGS. 8 and 9.

In the illustrated preferred form, the lever 37 is attached to the male connector piece 26 only along a connecting edge 40, and is free along its other sides. The lever 37 is thin enough and made of a sufficiently flexible material to enable it to be flexed inwardly in the direction indicated by arrow F (FIG. 3), out of the plane of the distal surface 34. To facilitate the inward movement of the lever 37, the body of the male connector piece 26 includes an open or routed out area 42 under the lever 37, which area 42 may extend through the entire body of the male connector piece 26, as illustrated. As shown, the lever 37 is biased normally in the unflexed position, so that it forms generally a portion of the distal surface 34 of the male connector piece 26.

In the preferred form of the invention shown in the figures, the lever 37 is integrally formed with the male connector piece 26. The lever 37 may be integrally formed by routing out the area 42 from the proximal surface 33 of the connector 26, and then cutting through to the distal surface in some suitable fashion along three sides of the routed out area 42. In alternate forms of the invention, the lever may be welded or soldered in place along its one connecting edge. In this latter form of the invention the body of the connector piece may be routed completely through from the distal surface to the proximal surface, or may be routed only partially through from the distal surface to create sufficient area for fixing the lever in position and for allowing the lever to flex inward. Also, the male connector piece may be manufactured in two pieces, an upper piece having the lever and routed-out area and a lower solid piece, the two pieces being welded together to form the connector piece according to the invention.

FIGS. 5, 6, and 7 show the female connector piece 27 according to the preferred form the invention, adapted for use with the male connector piece 26. The female connector piece 27 includes a body 48 mounted on a mounting plate 49 and having a receptacle 50.

The receptacle 50 is generally wedge-shaped and includes two opposing side surfaces 55, and a proximal surface 54, opposite a distal surface 53, the opposing surfaces being nonparallel and corresponding to the outer surfaces of the male connector 26. The outer surfaces of the body 48 of the illustrated female connector piece 27 also generally form a wedge shape with rounded edges, the walls which make up the body 48 being generally uniform in thickness. The receptacle 50 also has a relatively large front opening 57, and a relatively narrow back opening 58.

In the illustrated form of the invention, the body 48 of the female connector piece 27 also includes a lock aperture or opening 60 through a distal wall 61, from the distal surface 53 of the receptacle 50 to the outer surface 62. The lock opening 60 forms part of the locking means, the operation of which is discussed hereinafter with reference to FIGS. 8 and 9.

FIGS. 8 and 9 show the male connector piece 26 and the female connector piece 27 of the connector 25 in the connected position. In the connected position, the outer proximal 33, distal 34, and side 35 surfaces of the male connector piece 26 (FIGS. 2, 3, and 4) are adapted to substantially align with and abut the proximal 54, distal 53, and side surfaces 55 of the female connector piece 27 (FIGS. 5, 6, and 7). Thus, when fully inserted, there is virtually no play between the male connector piece 26 and female connector piece 27, the major outer surfaces of the male connector piece 26 and the major surfaces of the receptacle 50 of the female connector piece 27, being substantially abutted.

FIGS. 8 and 9 also illustrate a preferred locking means 66 in the locked or connected position, the locking means 66 in this form of the invention includes the lever 37, projection 38 routed area 42, and aperture 60. When the male connector piece 26 is fully inserted to the connected position as shown, the locking projection 38 on the lever 37 is adapted to snap into the aperture or opening 60 through the distal wall 61 of the female connector piece 27, thereby preventing the male end connector piece 26 from being withdrawn. Once the projection 38 has snapped into the opening 60, the male connector piece 26 may only be withdrawn after depressing the projection 38 out of the opening.

The illustrated locking means 66 has the substantial advantage of producing a secure connection between the force-supplying member and the patient's teeth, without having to tie the connector pieces together with ligature wire.

FIG. 9A shows an alternate connector 25a embodying the principles of the invention. This embodiment of the invention is similar to the connector 25 of FIG. 9, but includes an alternate locking projection 38a on the male connector piece and a corresponding alternate opening 60a in the female connector piece for receiving the alternate locking projection 38a as shown. In this form of the invention, the locking projection 38a has a wedge shape adapted to snap into the preferably rectangular alternate opening 60a. The rear portion of the projection 38a abuts the wall of the opening 60a in the illustrated locked position to prevent removal of the male connector piece. Similarly to the embodiment shown in FIG. 9, the projection 38a may simply be depressed out of the opening 60a to facilitate removal of the male connector piece from the connected position.

As previously discussed, the connector pieces will often times be angled with respect to each other prior to connection, particularly where the connection is to be active. However, as shown in FIG. 10, the unique wedge shape of the male connector piece 26 and the complementing wedge shape of the receptacle 50 of the female connector piece 27, allows easy insertion of the male connector piece 26, even when the male connector is angled somewhat with respect to the female connector piece 27 prior to insertion. In inserting the male connector piece 26 in the female connector receptacle 50, the relatively narrow outer end 30 of the male connector piece 26 enters the receptacle 50 through the relatively larger front receptacle opening 57. As shown in FIG. 10, a somewhat angled relationship (angle A) does not prevent the male connector piece 26 from being started into the receptacle 50 of the female connector piece 27. Once the narrow outer end 30 of the male connector piece 26 is started into the receptacle 50, the practitioner may simply press the two pieces together with an appropriate tool, and as they are pressed together, the two pieces automatically align with each other and the force-supplying member 21 flexes to apply the desired force. The rounded edges between the outer surfaces of the male connector piece 26 help prevent binding as the male connector is inserted into the receptacle 50.

According to the present invention, the act of inserting the male connector piece flexes the force-applying member 21 (FIG. 10). By contrast, previous orthodontic appliance systems required the orthodontist to flex the force-supplying member prior to making a connection to a particular tooth. This preflexing was not only very difficult, considering the small space in the patient's mouth in which to work, but was also generally uncomfortable to the patient.

Also, although the present appliance system is particularly useful where the connections are active, the system is also useful where the connection to the patient's teeth is passive. The unique shape of the male and female connector pieces according to the invention make unnecessary their careful alignment prior to connection. Such alignment was necessary with prior connector appliances.

FIG. 11 illustrates another appliance system 70 embodying the principles of the invention. The appliance system 70 includes a force-supplying member 71 and a connector appliance 72, the connector comprising a male connector piece 73 and a female connector piece 74.

In this embodiment, the force-supplying member 71 is a palatal bar, another intra-oral auxiliary appliance. However, in addition to use with auxiliary appliances such as the lingual arch in FIG. 1 and the palatal bar in FIG. 11, the connector appliance (25 in FIG. 1 and 72 in FIG. 11) according to the invention can be used with primary appliances, which are adapted for applying force to the buccal side of the patient's teeth. Also, auxiliary orthodontic members may be attached to the connector pieces or force-supplying member of the invention for performing various functions. Furthermore, although the appliance systems shown in FIG. 1 and 11 are adapted for substantially horizontal insertion of the male connector piece, the system may be adapted for vertical insertion of the male connector piece or insertion at any convenient orientation.

The above described preferred embodiments are intended to illustrate the principles of the invention, but not to limit the scope of the invention. Various other embodiments and modifications to these preferred embodiments may be made by those skilled in the art, without departing from the scope of the following claims.

What is claimed is:

1. A connector appliance for orthodontic appliance systems, said connector appliance comprising:
    a male connector piece having generally a wedge shape with a large base end and a relatively narrow outer end, the base end being adapted to be rigidly attached to a force-supplying orthodontic appliance,
    the male connector piece including four substantially planar outer surfaces, comprising two outer side surfaces forming opposite sides of the connector piece, and an outer proximal surface and an outer distal surface that also form opposite sides of the connector piece, said opposite outer side surfaces, and said opposite proximal surface and distal surface lying in nonparallel planes that slope closer together towards the narrow outer end of the male connector piece so that the outer end is narrower between said opposing surfaces than the larger base end, and
    a female connector piece being adapted to be rigidly attached to a patient's tooth and having a generally wedge-shaped receptacle with a large front opening and a relatively narrower back opening, the receptacle shape substantially corresponding to the wedge shape of the male connector piece so that the male connector piece can be received in the receptacle in a connected position, the receptacle of the female connector piece including four surfaces corresponding to the four outer surfaces of the male connector pieces, two side surfaces that form opposite sides of the receptacle, and the proximal surface and a distal surface that also form opposite sides of the receptacle, said opposing surfaces of the receptacle lying in nonparallel planes that slope closer together towards the relatively narrow back opening of the receptacle, and each of the four surfaces of the receptacle being adapted to substantially abut the corresponding outer surface of said male connector piece when said male connector piece is received in the receptacle in the connected position, and
    locking means associated with the male connector piece and the female connector piece for locking said connector pieces together in the connected position.

2. The connector of claim 1 wherein the locking means includes:
    an aperture extending through the distal surface of the female connector receptacle, the aperture being adapted to receive a locking projection connected the male connector piece when the male connector piece is inserted in the receptacle to the connected position, and
    biasing means connected to the male connector piece for biasing the locking projection into the aperture when the male connector piece is inserted in the receptacle to the connected position, and for enabling the projection to be retracted from the aperture so that the male connector piece can be removed from the connected position.

3. The connector appliance of claim 2 wherein the biasing means is contained within a cavity in the distal surface of the male connector piece and includes a spring loaded lever connected at one end to the male connector piece and adapted to move from a biased position to a retracted position within the cavity.

4. The connector appliance of claim 1 wherein the female connector piece is adapted to be attached directly to a tooth with a suitable adhesive.

5. The connector appliance of claim 1 including an attachment band adapted to be positioned tightly around each tooth to which a desired force is to be applied, and wherein the female connector is adapted to be attached to the attachment band.

6. An orthodontic appliance system comprising:
    a force-supplying member adapted to fit inside a patient's mouth to supply a desired force to at least two of the patient's teeth,
    at least two male connector pieces rigidly attached to the force-supplying member, each male connector piece being generally wedge-shaped and having a large base end attached to the force-supplying member and a relatively narrower outer end,
    each male connector piece includes four substantially planar outer surfaces, two outer side surfaces forming opposite sides of the connector piece, and an outer proximal surface and an outer distal surface, which also form opposite sides of the connector piece, said opposite outer side surfaces, and said opposite proximal surface and distal surface lying in nonparallel planes that slope closer together towards the narrow outer end of the male connector piece so that the outer end is narrower between said opposing surfaces than the larger base end,
    a corresponding female connector piece for each male connector piece, each female connector piece being adapted for rigid attachment to one of the patient's teeth, and having a generally wedge-shaped receptacle with a large front opening at one end tapering to a relatively narrow back opening at the opposite end, each receptacle substantially corresponding in shape to the shape of one of the male connector pieces so that said corresponding male connector piece can be received therein in a connected position, the male connector piece substantially abutting the wedge-shaped receptacle in said connected position, the receptacle of the corresponding female connector piece includes four surfaces corresponding to the four outer surfaces of the male connector piece, two side surfaces that form opposite sides of the receptacle, and a proximal surface and a distal surface that also form opposite sides of the receptacle, said opposing surfaces of the receptacle lying in nonparallel planes that slope closer together towards the relatively narrow end of the receptacle, and each of the four surfaces of the receptacle being adapted to substantially abut the outer surfaces of said male connector piece when said male connector piece is received in the receptacle in the connected position, and locking means associated with each male connector piece and the corresponding female connector piece for locking said connector pieces together in the connected position, whereby each female connector piece may be rigidly attached to one of the patient's teeth and the force-supplying member may be positioned in a patient's mouth with each male connector piece received in a different female connector piece in the connected position so that the force-supplying member can supply a desired force to each said tooth.

7. The orthodontic appliance system of claim 6 wherein each locking means includes:

an aperture extending through the distal surface of the female connector receptacle, the aperture being adapted to receive a locking projection connected to the male connector piece when the male connector piece is inserted in the receptacle to the connected position, and biasing means connected to said male connector piece for biasing the locking projection into the aperture when said male connector piece is inserted in said receptacle to the connected position, and for enabling the projection to be removed from the aperture so that said male connector piece can be removed.

8. The orthodontic appliance system of claim 7 wherein the locking projection is generally wedge shaped and slopes in the same direction as the wedge shape of the male connector piece.

9. The orthodontic appliance system of claim 6 wherein the female connector piece is adapted to be attached directly to a tooth by a suitable adhesive.

10. The orthodontic appliance system of claim 6 including an attachment band adapted to be positioned around each tooth to which a desired force is to be applied, and wherein the female connector is adapted to be attached to the attachment band for providing corrective force to the tooth.

11. The orthodontic appliance system of claim 6 wherein said force-supplying member is substantially rigid and has a preselected length and shape to fit the patient's mouth.

12. A method for applying a force inter-lingually to at least two teeth of a patient, said method comprising the steps of:

a. affixing a female connector piece to the lingual side of each of said at least two teeth, said female connector piece defining a generally wedge-shaped receptacle with a large front opening and a relatively narrower back opening, the receptacle of the female connector piece including two side surfaces that form opposite sides of the receptacle, and a proximal surface and a distal surface that also form opposite sides of the receptacle, said opposing surfaces of the receptacle lying in nonparallel planes that slope closer together towards the relatively narrow back opening of the receptacle, b. measuring the distance between said female connector pieces affixed in step a., c. shaping a substantially rigid force-supplying member of a length that corresponds to the distance measured in step b., d. affixing at least two male connector pieces to the shaped force-supplying member of step c., said male connector piece defining generally a wedge shape with a large base end and a relatively narrow outer end, the base end being adapted to be rigidly attached to a force-supplying member, the male connector piece including four substantially planar outer surfaces, two outer side surfaces forming opposite sides of the connector piece, and an outer proximal surface and an outer distal surface that also form opposite sides of the connector piece, said opposite outer sides surfaces, and said opposite proximal surface and distal surface lying in nonparallel planes that slope closer together towards the narrow outer end of the male connector piece so that the outer end is narrower between said opposing surfaces than the larger base end, the wedge shape substantially corresponding to the receptacle shape of the female connector piece so that the male connector piece can be received in the receptacle with the four surfaces of the male connector piece abutting the four interior surfaces of the receptacle in a connected position, and e. inserting each of said male connector pieces affixed to the force-supplying member in step d. into a corresponding one of said female connector pieces affixed to the patient's teeth in step a.

13. The method for applying a force inter-lingually to at least two teeth of a patient as in claim 12 wherein the distance measured in step b. for the lower mouth is the lingual distance between the at least two teeth, and for the upper mouth is either the lingual distance or the palatal distance depending on the separation of the at least two teeth and the desired placement of the force-supplying member.

* * * * *